(12) United States Patent
Witchey

(10) Patent No.: US 12,085,571 B2
(45) Date of Patent: Sep. 10, 2024

(54) BIOLOGICAL DEPOSIT LABELING AND TRACKING INCLUDING ISOTOPE, RARE EARTH METAL OR MITOCHONDRIA TAGS

(71) Applicant: ImmunityBio, Inc., Culver City, CA (US)

(72) Inventor: Nicholas J. Witchey, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 1134 days.

(21) Appl. No.: 16/893,213

(22) Filed: Jun. 4, 2020

(65) Prior Publication Data
US 2020/0392577 A1 Dec. 17, 2020

Related U.S. Application Data

(60) Provisional application No. 62/860,977, filed on Jun. 13, 2019.

(51) Int. Cl.
*G01N 33/58* (2006.01)
(52) U.S. Cl.
CPC ......... *G01N 33/58* (2013.01); *G01N 2458/40* (2013.01)
(58) Field of Classification Search
USPC .......................................................... 702/19
See application file for complete search history.

(56) References Cited

U.S. PATENT DOCUMENTS

| 8,507,222 | B2 | 8/2013 | Wong et al. |
| 10,138,462 | B2 | 11/2018 | Klingemann |
| 10,456,420 | B2 | 10/2019 | Lee et al. |
| 2016/0089388 | A1 | 3/2016 | Levitt |
| 2020/0009259 | A1 | 1/2020 | Wu et al. |

FOREIGN PATENT DOCUMENTS

| GB | 2598259 A | * | 2/2022 | ............. A61B 1/041 |
| WO | 2018057520 A1 | | 3/2018 | |
| WO | 2019/089561 A1 | | 5/2019 | |

OTHER PUBLICATIONS

Korch, Christopher, et al. "Authentication of M14 melanoma cell line proves misidentification of MDA-MB-435 breast cancer cell line." International journal of cancer 142.3 (2018): 561-572. (Year: 2018).*
Korch Supplemental "Authentication of M14 melanoma cell line proves misidentification of MDA-MB-435 breast cancer cell line." International journal of cancer 142.3 (2018): 561-572. (Year: 2018).*
Romano, Paolo, et al. "Cell Line Data Base: structure and recent improvements towards molecular authentication of human cell lines." Nucleic acids research 37.suppl_1 (2009): D925-D932. (Year: 2009).*
Capes-Davis, Amanda, et al. "Match criteria for human cell line authentication: where do we draw the line ?." International journal of cancer 132.11 (2013): 2510-2519. (Year: 2013).*
Prange, Andreas, and Daniel Pröfrock. "Chemical labels and natural element tags for the quantitative analysis of bio-molecules." Journal of Analytical Atomic Spectrometry 23.4 (2008): 432-459. (Year: 2008).*

* cited by examiner

*Primary Examiner* — G. Steven Vanni
(74) *Attorney, Agent, or Firm* — Priti Phukan; Umberg Zipser LLP

(57) ABSTRACT

Methods and systems are provided herein to track an original biological deposit that is withdrawn from a public repository. In some aspects, the public repository may include the ATCC or any other public repository in which biological materials are deposited for access by the general public. These techniques may be used to identify a product or biological deposit from a third party that is derived from the original biological deposit.

12 Claims, 9 Drawing Sheets

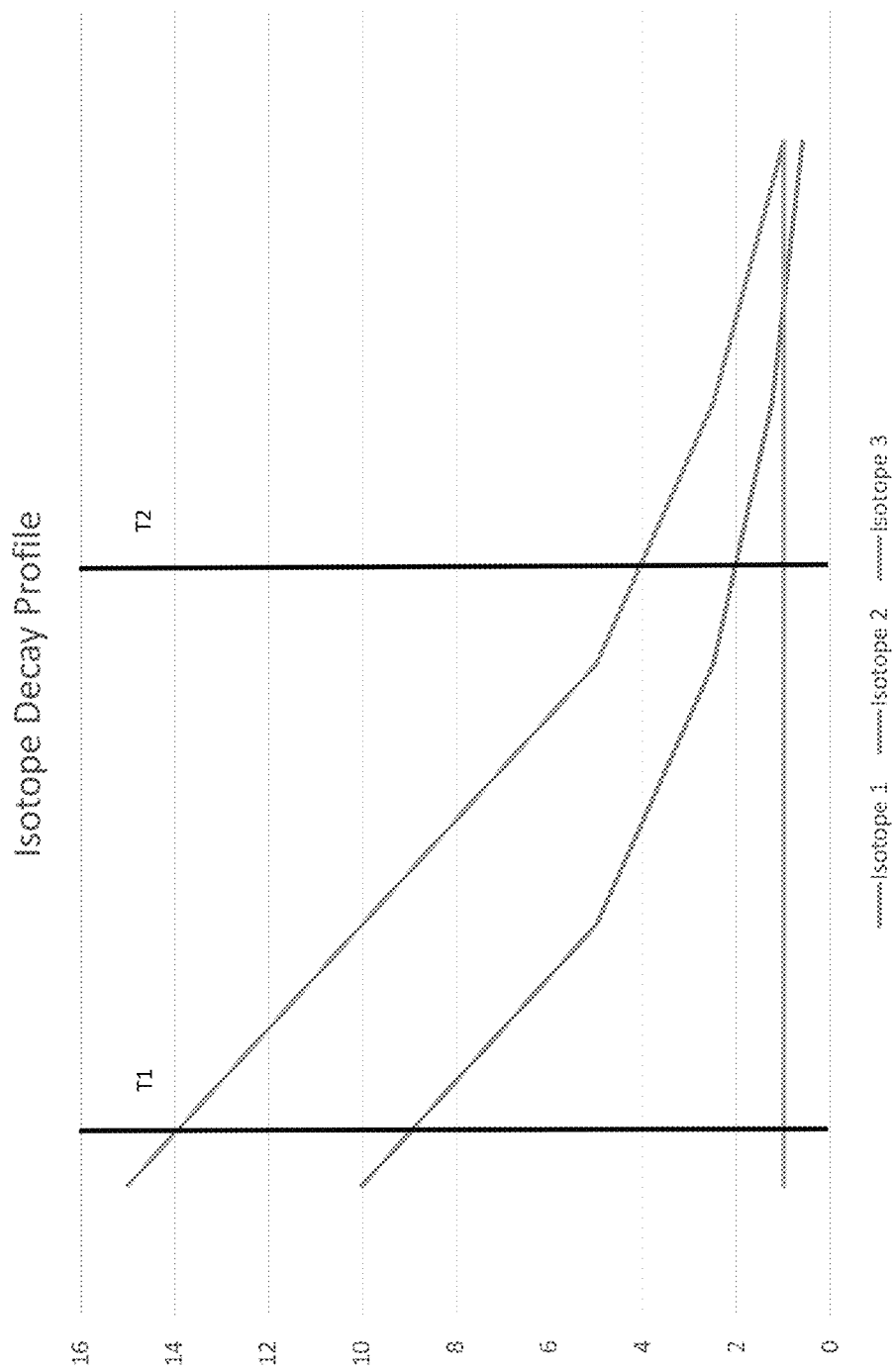

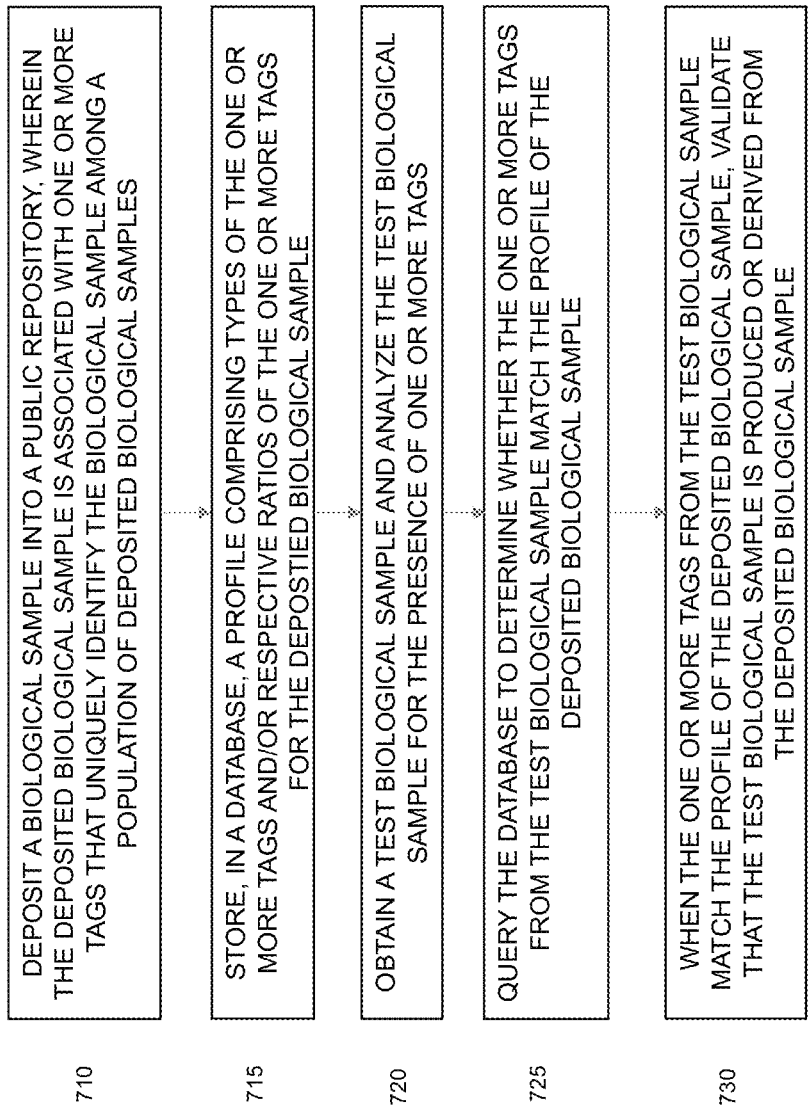

BIOLOGICAL DEPOSIT LABELING AND TRACKING INCLUDING ISOTOPE, RARE EARTH METAL OR MITOCHONDRIA TAGS

This application claims priority to U.S. provisional patent application with the Ser. No. 62/860,977, which was filed Jun. 13, 2019, which is incorporated by reference herein in its entirety.

FIELD OF THE INVENTION

The field of the invention is technologies associated with tracking of biological materials, and in particular, tracking of biological deposits upon exiting a public repository to identify biological products or cell lines manufactured from or derived from the biological deposit.

BACKGROUND

This background description includes information that may be useful in understanding the systems and methods described herein. It is not an admission that any of the information provided herein is prior art, or that any publication specifically or implicitly referenced is prior art.

In order to meet certain patentability requirements, a biological deposit sometimes is required to be placed in a publically accessible international depositary authority (IDA) (e.g., such as the American Type Culture Collection (ATCC) repository, etc.) in accordance with the rules of the Budapest Treaty. For example, a cell line may be deposited to meet written description and/or enablement requirements. Other examples of materials which may be required to be deposited include, but are not limited to: viruses, phages, plasmids, symbionts, yeast, and replication defective cells.

Generally, public repositories do not track who accesses the repository to obtain the biological deposit. While withdrawals of biological deposits are permitted for research purposes, it is possible that the biological deposit may be used in an unauthorized manner to make a commercial cell line or biologic based on, or derived from, the biologic deposit. In some cases, it may be possible to obtain information about who accesses the deposit, but information regarding the use of the deposit is not available.

Genomic labels (e.g., inserted using CRISPR/Cas9) have been used to tag cells. However, this approach is problematic for biologic deposits, as the integrity of the deposited cell line covered by a patent may be compromised if the insertion occurs within the coding region of an expressed therapeutic.

In other cases, detectable iron oxide particles may be used to label the cells, but this technique is often relatively short-lived, as the cells lose the majority of the iron oxide during the first few rounds of cell passage.

Thus, there remains a need for tracking and verification methods and systems to detect unauthorized commercial use of a biologic deposit.

SUMMARY OF THE INVENTION

Methods and systems to track biological deposits that are withdrawn from a public repository are provided. The public repository may be the ATCC or any other public repository in which biological materials are deposited for access by the general public, for example any repository depositary institutions that has acquired the status of International Depositary Authority under the Budapest Treaty for the International Recognition of the Deposit of Microorganisms for the Purposes of Patent Procedure ("the Budapest Treaty.")

A biological deposit may be in one or more containers, and may be in any suitable form, including frozen, lyophilized, solid, liquid, Formalin-Fixed Paraffin Embedded (FFPE) tissue, etc.

A biological deposit may refer to, but is not limited to, a self-replicating organism such as prokaryotic or eukaryotic cells, such as therapeutic cells (e.g., T cells, NK cells, NK-92 cells, B-cells, stem cells, iNKT cells, CAR-T cells, yeast-based vaccine vehicles, etc.), as well as indirect cell replicating materials such as viruses, retro-viruses, associated viruses, phages, plasmids, symbionts, replication defective cells, etc. Specific examples of cells that may be deposited include cells used in large or small scale manufacturing processes or for research purposes (e.g., CHO cells, cells used to express recombinant adenoviruses, COS cells, HeLa cells, EC-7 cells, NCI-60 cells, HEK-293 cells, hybridomas, etc.) or any other suitable cell line used for manufacturing a biologic, such as proteins, antibodies, gene therapies, or vaccines (e.g., cancer vaccines, viral vaccines, etc.). The methods and systems described herein may be used to label or tag any such biological material.

In one aspect, methods and systems are provided for tagging cells of a cell line. Advantageously, the tag is a persistent tag that is detectable after multiple rounds of cell passage (e.g., passages associated with a culturing or manufacturing process). Tags preferably do not compromise the genomic integrity of the cell line or affect the product produced by the cell line. Accordingly, the characteristics of the cell line or of the product are commensurate with or without the tags. Further, the combination of tags needs to be retained in its respective cell line at a sufficient level to determine tag ratios and, in the case of radioisotopes, the age of the cells. In general, the tag(s) will not react with or change the properties of the biological sample being deposited.

In some aspects, these techniques may be used to identify a cell line that has been withdrawn from a repository. In other aspects, these techniques may be used to identify products produced by a cell line that has been withdrawn from a repository. In some cases, tags, such as radioisotope tags, may be used to date the cell line, to determine the date or approximate date of deposit, as well as identify the cell line.

In some cases, tags may include, but are not limited to, one or more dyes, radioisotopes, performs, exosomes, organelles, mitochondria, proteins, nanoparticles, DNA barcodes, liposomes, heavy metals, primers, etc. In other aspects, the tags may be encapsulated in a structure conjugated to a linker (e.g., an aldox linker; see published US patent application US20160089388), to deliver the tags to the cell (e.g., a linker on a nanoparticle may deliver radioisotopes to cells, etc.). Other elements that may be used for tagging include aragonite.

Cells may be tagged using any suitable method. For example, intracellular tags may be taken up by endocytosis or via diffusion using the cell membrane. Alternatively, transfection techniques may be used to introduce intracellular tags to the cell. For example, tags may be encapsulated into nanoparticles and introduced into the cell via transfection methods that are well known in the art. Extracellular tags that bind to the surface of the cell membrane (e.g., such as dyes) or tags that are embedded in the cell membrane may also be used. Alternatively, liposomes may fuse with the cell membrane to release tags into the interior of the cell. A variety of tags are known in the art, and all such techniques are contemplated for use herein.

Given that a radioisotope decays according to a predefined trajectory based on its respective half-life, which can be represented by statistical analysis of a population of the radioisotope, the amount of each radioisotope and the respective ratios of the radioisotopes relative to each other may be predicted as a function of time. In cases in which individual radioisotopes are not able to be detected, a composite decay rate may be determined for a mixture of two or more independently decaying radioisotopes with different half-lives. This approach may be used as an alternative to mass spectrometry for cases in which a relatively small number of radioisotopes with different half-lives are used as tags.

In some aspects, for nanoparticles that contain radioisotope tags, it is assumed that the radioactive signature (e.g., which may include one or more of the radioisotope type, radioisotope concentration, and respective radioisotope ratios) is relatively uniform throughout the population of nanoparticles, and that the radioisotopes remain encapsulated within the nanoparticle throughout the biological deposit life cycle, which includes tagging, deposit, withdrawal, and analysis. Accordingly, the radioisotope signature may be predictable based upon the number of cell divisions (e.g., as with each division, the concentration of the nanoparticles within the two daughter cells may be approximately half of the parent cell). Thus, a plurality of different radioisotopes may be used to tag a cell line in order to generate a radioactive signature for identification and tracking of the deposited cell line. In other cases, the radioisotopes may be incorporated into the product generated by the cell line to identify the corresponding deposited cell line.

In cases in which statistical modeling of the tags may be difficult, the biological deposit may be experimentally evaluated as a function of time in order to determine ratios and concentrations as a function of time. For example, a biologic deposit may be made, withdrawn by the depositor, and assayed for the presence and amount of tags (e.g., radioisotopes) as a function of time.

In other aspects, the present techniques may also be helpful for ensuring viability of the biological sample prior to administration to a patient. For personalized medicine, the biological sample may be analyzed to indicate an age of the sample, and where the sample has aged past a predetermined threshold time, the therapeutic may not be administered to the patient. In other aspects, for radioisotope tags, the radioactivity should be below a threshold before administering the biological sample (e.g., therapeutic) to the patient. Similarly, non-radioactive isotopes may be used to tag cells, and a non-radioisotope signature may be analyzed by mass spectrometry or any other suitable measurement device.

In other embodiments, molecules may be added to downregulate replication of the biologic deposit, for example, myeloid-derived suppressor cells (MDSCs). A class 1-specific histone deacetylase (HDAC) inhibitor, such as entinostat, may be added to MDSCs to suppress the ability of these cells to replicate as well as their activity, in an effort to limit both the number and activity of MDSCs (and T regulatory cells), in an effort to impair unauthorized commercial use of the biologic deposit.

In other embodiments, tags may be added to detect infringement of patents directed to products of the biologic deposit. For example, a deposited CHO cell line modified to produce N-803 may be tagged with non-radioactive or radioactive isotopes. The CHO cell line, when expressing the N-803 product (an IL-15 variant having an N72D mutation; see U.S. Pat. No. 8,507,222), may produce a labeled N-803 molecule comprising isotopes or a subset of isotopes present in the CHO cell. Thus, the CHO cell line may be identified with a specific isotope signature and predetermined ratios of the isotopes, while the product of the CHO cell line may be labeled with isotopes that are incorporated into the product. The product of the CHO cell line may have a specific isotope signature with a potentially different isotope ratio, as compared to the CHO cell line, based on the extent of uptake of the isotopes into the product.

Various objects, features, aspects, and advantages of the subject matter described herein will become more apparent from the following detailed description of preferred embodiments, along with the accompanying drawing figures in which like numerals represent like components.

BRIEF DESCRIPTION OF THE DRAWINGS

FIG. 4 is a graphical illustration of radioisotope decay as a function of time, according to embodiments of the techniques disclosed herein.

FIG. 5 represents an operational flowchart of tracking biological samples, according to embodiments of the techniques disclosed herein.

DETAILED DESCRIPTION

Figure 1B:
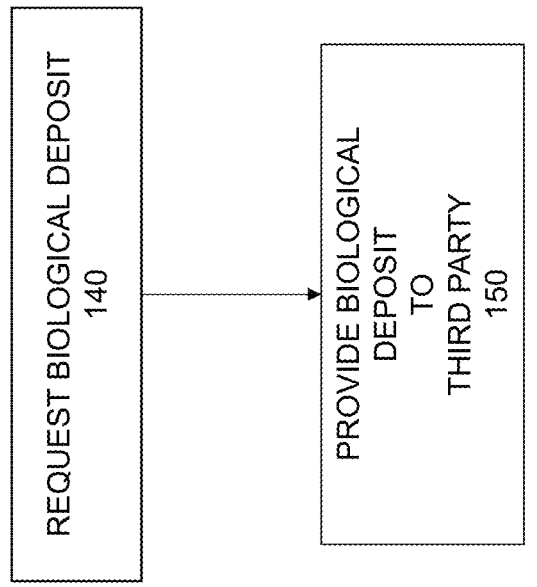
FIG. 1B is a flowchart of requesting the biological deposit by a third party, according to an embodiment of the techniques disclosed herein.

To meet patentability requirements, biologics are often required to be deposited in a public repository, such as the ATCC, EuMMCR, UK Stem Cell Bank, or other depository; allowing the public access to the biologic. Most repositories do not track acquisition of deposits by third parties. Even if deposits are tracked, detection of non-research uses by the acquiring third party company is still difficult. Accordingly, techniques are needed to track biological deposits such as cell lines and the products produced by the cell lines after leaving the repository.

In general, any suitable biologic material may be deposited in the ATCC, including, but not limited to, microorganisms, mixed cultures, cell lines, and hybridomas, plasmids and vectors, animal viruses, plant tissue cultures, and seeds, etc. In some embodiments, the cell line is a therapeutic that may be administered to a patient, such as an NK cell (e.g., NK-92, haNK, taNK, aNK, etc.), a CAR T-cell, a modified T cell, stem cell, etc. In other embodiments, the cell line may produce a therapeutic (e.g., a hybridoma that produces a mAb, etc.). An example NK-92 cell line that relies on an ATCC cell deposit and could benefit from the disclosed techniques is described in co-owned U.S. Pat. No. 10,138,462 or in U.S. Pat. No. 10,456,420. The techniques provided herein are suited to track any biological material deposited within a repository for tracking after withdrawal from the repository.

With these approaches, cell lines may be tagged with high specificity without compromising the actual genomic structure (DNA) of the deposited cell line. Further, cells used for commercial purposes can be traced back to the original biological deposit.

In general, the present techniques may be used to track any suitable type of biological deposit, including but not limited to, therapies that include and/or are derived from NK cells, T cells, stem cells, B cells, dendritic cells, stem cells, viruses, yeast, recombinant organisms, bacterial vaccines, gene therapies, personalized medicine, etc. For example, vaccines may be produced by yeast, E. coli, etc. which may be tagged according to the techniques provided herein. Organisms such as E. coli may be used to produce biofuels, and these organisms may also be labeled or tagged by the techniques provided herein.

A life cycle of a biological deposit with reference to present techniques may include labeling the biological material, depositing the biological material by the owner, obtaining the biological material by a third party, and detecting use of the biological material by the third party for non-research purposes (e.g., such as producing a therapeutic or a modified version of a therapeutic from the obtained biological deposit) by the owner. If the third party makes a biological deposit or offers the product for sale, the biologic may be obtained and tested for the type and/or ratio of various tags, such as radioisotopes.

One of skill in the art will appreciate that the disclosed techniques provide many advantageous technical effects including the ability to track a biological deposit and/or product of the biological deposit (e.g., a cell line or product of a cell line) obtained for research purposes or track biological deposits through a logistics lifecycle. If the tags are matched to a signature in a database, this may provide evidence that the biological deposit provided by the third party was derived from the biological deposit of the owner. Accordingly, the present techniques greatly improve the ability for a depositor to detect misuse and infringement of their deposited biological materials.

FIGS. 1A-1D show aspects of a life cycle of a deposited biological sample. In reference to FIG. 1A, at operation 110, a biological sample is generated by the owner (e.g., a cell line, a hydridoma, a plasmid, etc.). At operation 120, the biological sample is labeled or tagged according to the techniques provided herein to generate a labeled biological sample. Tags may include any suitable tag such as dyes, radioisotopes, heavy metals, primers, etc. At operation 130, the labeled biological sample 130 is deposited into a repository such as the ATCC.

FIG. 1B shows a flow chart of obtaining a deposit by a third party from a repository. At operation 140, a request is received for the biological deposit. The biological deposit may be obtained from the repository in any suitable form, including but not limited to, frozen form, cultured form, lyophilized form, as seeds, etc. At operation 150, the biological deposit is provided to the third party.

Figure 1A:
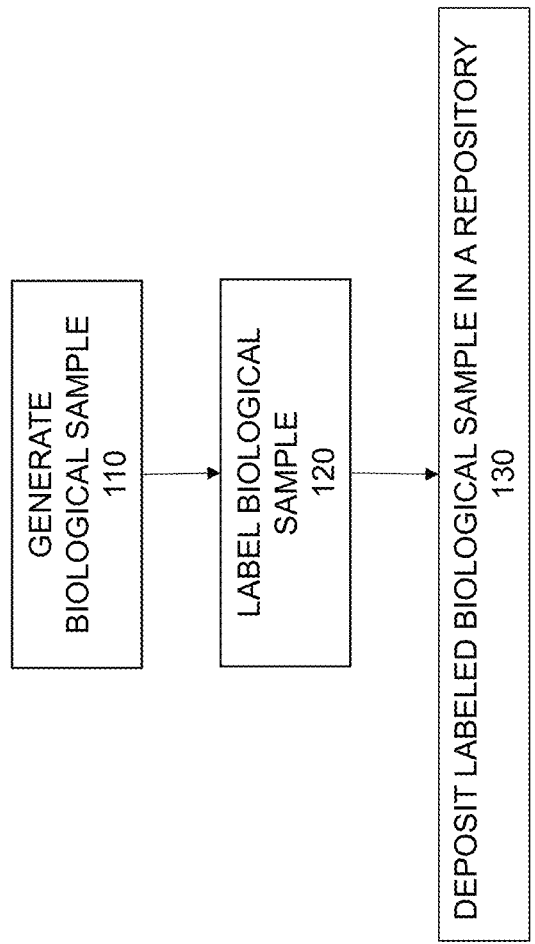
FIG. 1A is a flowchart showing depositing a biological sample in a public repository, according to an embodiment of the techniques disclosed herein.
Figure 1C:
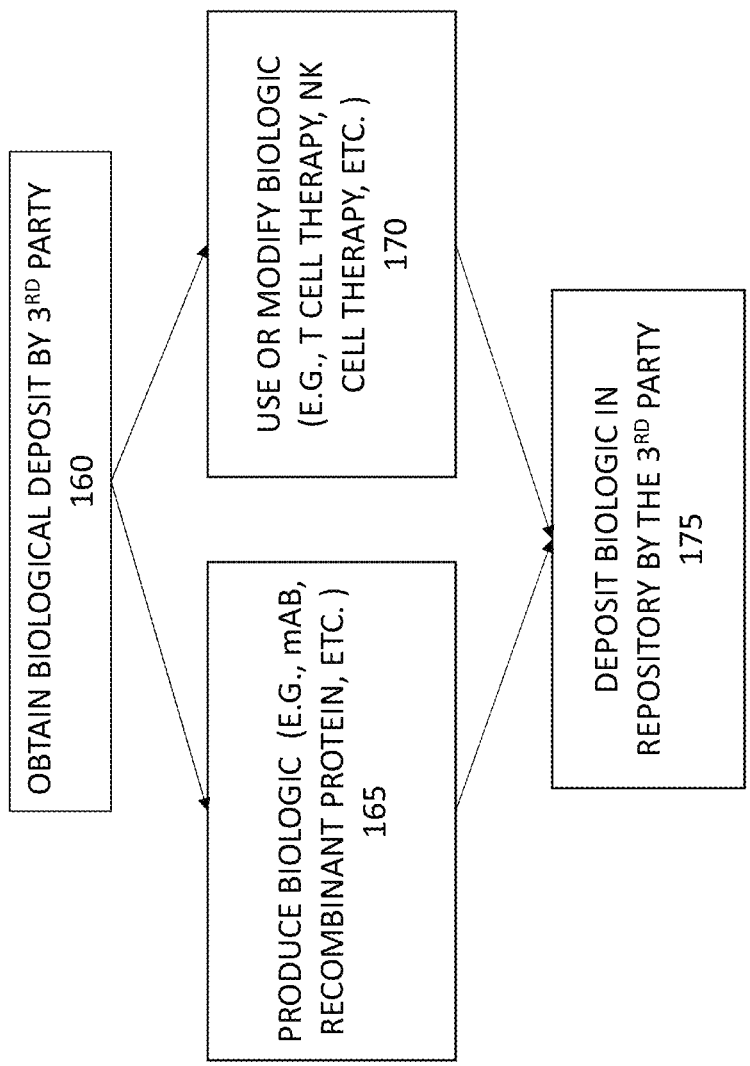
FIG. 1C is a flowchart of producing a biologic from the biological deposit by a third party, according to an embodiment of the techniques disclosed herein.

FIG. 1C shows an example process of a third party obtaining a biological deposit and using the biological material for commercial use. At operation 160, the third-party who obtains the biological deposit may use the biological material for research purposes. However, in some cases, the third party may produce a biologic product from or derived from the obtained biological deposit to use for commercial use, as shown at operation 165, counter to a withdrawal agreement. In other cases, the third party may produce a cell line from or derived from the received biological deposit to use for commercial use, at operation 170. At operation 175, the biologic (e.g., cell line) is deposited in a public venue by the third party.

Figure 1D:
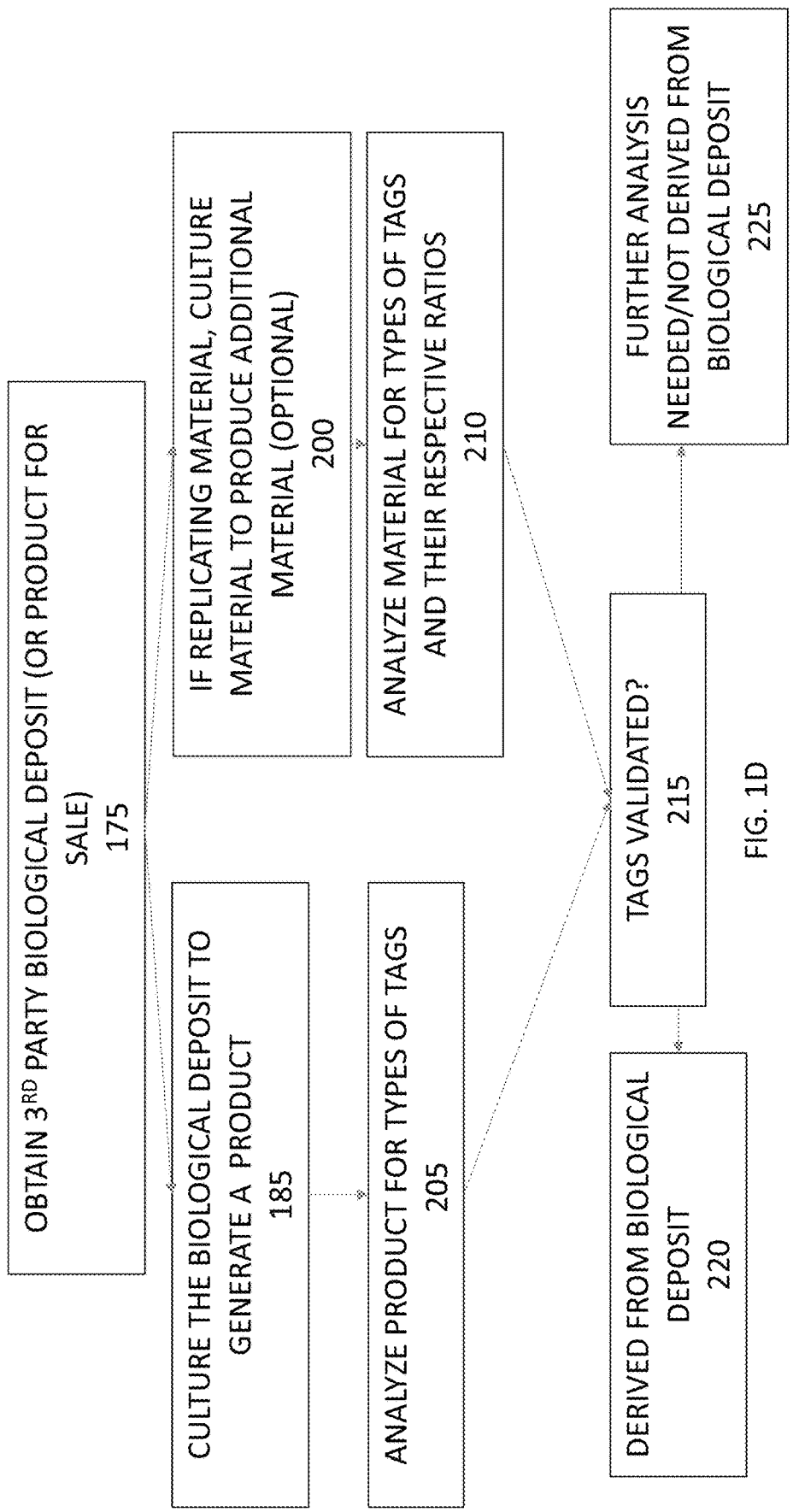
FIG. 1D is a flowchart of obtaining the biological deposit from the third party and testing for the presence of tags, according to an embodiment of the techniques disclosed herein.

FIG. 1D shows an example process of testing a biological deposit from a third party to ascertain whether the biological deposit was derived from the original biological deposit (see, FIG. 1A, operation 130). At operation 175, the biological deposit from the third party is obtained. At operation 185, the biological deposit is cultured to generate a product (e.g., expression of a product by a cell line). The product is analyzed for the presence of tags at operation 205. Similarly, if the biological deposit can replicate, it may be cultured at operation 200 to produce additional materials (e.g., cells). The biological material may be analyzed for the presence of tags and respective ratios of different tags at operation 210.

At operation 215, a database system may be searched for the combination of identified tags and/or their respective ratios to determine whether the tags match a tag or a combination of tags in a database for a biological deposit. It is understood that the database may contain models of ratios of isotopes and corresponding rates of decay. In some embodiments, a user may not know the age of the sample that is being tested. Therefore, the database may be searched for a specific combination of tags. The system may also be searched for specific ratios of isotopes, wherein the specific ratios are provided as a function of time based on rates of radioactive decay. For example, for two radioisotopes having a 2:1 ratio, the database may contain trajectories of the rate of decay for each isotope as a function of time, and the ratios may change if the rates of decay are substantially different. Thus, in this example, the database may be searched for the first radioisotope and the second radioisotope, as well as a value of the first trajectory and the second trajectory at a point in time that matches the observed concentrations of the first isotope and the second isotope. In other cases, the database may store the two types of isotopes and a series of ratios of the two isotopes reflecting radioactive decay as a function of time. The system may be searched for the two types of isotopes and a matching ratio of the isotopes. All practical number of isotopes and ratios are contemplated.

If the system validates the tags, finding that the tags are present, then the system concludes at operation 220 that the biological material from the third party deposit is derived from a biological deposit (see, FIG. 1A, operation 130). At operation 225, if the system is not able to validate the tags, further analysis may be needed or the system may be able to rule out that the biological material was derived from the biological deposit.

Figure 1E:
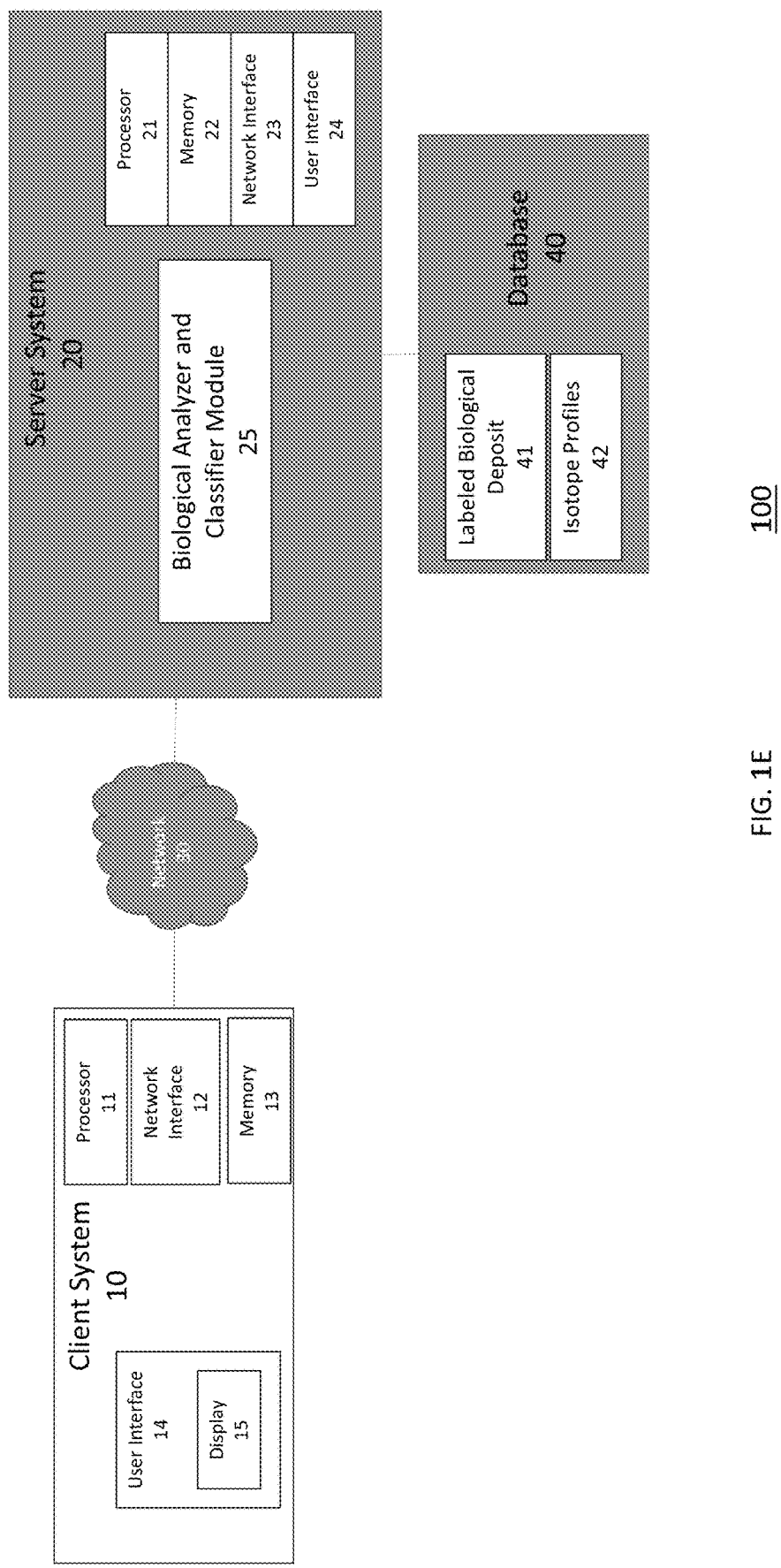
FIG. 1E shows an example computing environment.

FIG. 1E shows an example computing environment that may be used to identify labeled or tagged biological deposits according to the techniques provided herein.

The computing environment may comprise a client system 10 connected to a server system 20 by a network 30. Server system 20 and client system 10 may be remote or local to each other and may communicate over any suitable network 30 (e.g., a wide area network (WAN), local area network (LAN), Internet, Intranet, hardwired, wireless, etc.).

Client system 10 may comprise at least one processor 11, a network interface 12, and at least one non-transitory, computer readable memory 13, as well as a user interface 14 and a display 15 for displaying results of the analysis. Server system 20 may comprise a processor 21, a memory 22, a network interface 23, and a user interface 24. The user interface 14 may be used to submit information pertaining to identified tags associated with a biological material. For example, a user through the user interface 14 may enter various radioisotopes and ratios of radioisotopes, as determined experimentally for a biological sample. This information may be used to query the server system 20, using biological analyzer and classifier module 25 to determine whether a matching labeled biological deposit 41 and isotope profile 42 are found. If a match is found, the system will provide the results to the client system 10 for user review and analysis. Based on the isotopes provided and the ratios, the system may identify a match and notify the user when a match is found.

Database 40 is considered a computing device (e.g., a server, cloud, etc.) able to store and retrieve data records based on an indexing scheme an may be implemented by any conventional or other database software and may communicate with server system 20 over any suitable media and protocol including LAN, WAN, hardwire, wireless, Internet, Intranet, etc. Labeled biological deposit 41 may contain a record for each biological deposit indicating one or more types of biological tags and initial ratios or concentrations of these tags. In some cases, the tags (e.g., radioisotopes) may change as a function of time. For example, two radioisotopes may decay at different rates as a function of time, and therefore, the ratio of these two isotope may change as a function of time. Accordingly, for each labeled or tagged biological deposit 41 with isotopes that decay over time, a corresponding model of the radioactive decay for the one or more tags may be provided in isotope profiles 42. The isotope profiles may be simulated, based upon known half-lives, or for complex systems, the half-lives may be experimentally determined. These profiles may be searched to determine whether a matching ratio is found over a specified time range. In some embodiments, the profiles can comprise estimated ratio signatures as a function of time. Thus, a single tagged cell line profile might have multiple ratio signatures for different times, possibly estimated at time periods corresponding to days, months, or years after deposit. A measured signature can then be compared against such estimated ratio signatures to identify which estimated ratio signature is closest to the measured signature.

Server systems 20 and client systems 10 may be implemented by any conventional or other computer system as well as any commercially available or custom software including server/communication software, browser/interface software, and custom modules to analyze and classify the biological deposit information to determine whether or not the tags/ratios match a known labeled biological deposit.

Radioisotopes

In some embodiments, a mixture of radioisotopes may be used to tag the cell. Many different radioisotopes are known in the art, and any suitable combination may be used. Half-lives of radioisotopes may range from yoctoseconds to minutes, days, months, years, decades, and even longer. For the purposes of present embodiments, half-lives of radio isotopes may be in the range of days to months to years to provide a range of tracking options over a wide range of time (e.g., 20 years or longer, over the life of the ATCC deposit, lifetime of corresponding patents, drug or biological exclusivity terms, etc.). In some cases, radioisotopes with different half-lives may be used to tag the cells, including a tag with a half-life of days, a tag with a half-life of months, a tag with a half-life of years, a tag with a half-life of decades, or any combination thereof.

Any number of isotopes may be used to tag a cell, including 1 to 50 isotopes, 1 to 40 isotopes, 1 to 30 isotopes, 1 to 20 isotopes, 1 to 10 isotopes, 5 to 10 isotopes, 5 to 20 isotopes, or any number in between, etc. In some cases, the isotopes may be present in different ratios relative to each other. Isotope ratios may range from 1:1 to 1:100, from 1:2 to 1:100, from 1:4 to 1:100, 1:5 to 1:100, from 1:10 to 1:100, 1:20 to 1:100, from 1:25 to 1:100, from 1:50 to 1:100, from 1:1 to 1:50, 1:1 to 1:25, from 1:1 to 1:10, from 1:1 to 1:5, 1:1 to 1:4, from 1:1 to 1:3 from 1:1 to 1:2, or any range in between. Using a larger number of isotopes provides for a larger body of possible ratio signatures. For example, two isotopes would provide for a single ratio, which would be suitable for a single cell deposit. The ratio could be adjusted to create different ratios to provide different ratio signatures for different deposits. Further, three isotopes would provide for three ratios, which would provide for a greater multiplicity of possible ratio signatures as discussed further below.

In some embodiments, each isotope may have a different half-life, falling within different ranges of time (e.g., minutes, months, years, decades, etc.). In general, when a biological deposit is obtained and cultured, the concentration of the radioisotope may decrease as a function of time relative to the number of cell division cycles that the cell undergoes, whether the radioisotopes are in free form or encapsulated within a nanoparticle.

In some cases, radioisotope decay may be complex, and the depositor of the biologic deposit may conduct a series of experiments over a period of time with the biologic material to generate experimental profiles of the radioisotopes as a function of time. This information may be used to validate tags (e.g., at operation 215 of FIG. 1D). For example, labeled cell lines may be assayed for the presence of different labels and ratios of the labels, wherein each isotope has a different half-lives. In general, the biological sample undergoing cell culture to generate experimental profiles may be sampled multiple times during a given time period to generate the radioisotope profile.

In other cases, predictive models may be developed to predict radioisotope profiles as a function of time, based on published data regarding half-life and/or published information regarding decreases in radioisotope levels during cell culture as a function of time.

The combination of radioisotopes (e.g., type and/or ratios) provides a unique radioactive signature with which to identify the biological deposit. In some cases, the concentration of the radioisotope may be used to determine a timeframe from which the cells were withdrawn from the deposit.

As an example, if up to 10,000 samples may be stored in a repository, then the number of tags (e.g., in this case, radioisotopes) that should be added for a unique signature may be determined by r!(n-r!) where r is the number of radioisotopes selected, and n is the total available space of the radioisotopes. For twenty different radioisotopes that are approved for use (e.g., by the FDA), any five of these twenty radioisotopes may be added to the biological sample to generate a unique signature. Selecting any five radioisotopes of a total of twenty possible radioisotopes (and assuming the same radioisotope is not selected more than once) generates over 18,000 different radioisotope signatures. One of skill in the art should appreciate that this represents one possible use of radioisotopes to create relevant ratio signatures. It is also contemplated that two isotopes could be used to create a range of measurable ratio signatures to achieve a desired coverage of a number of cell deposits.

In further contemplated aspects, it should be appreciated that tagging with radioisotopes and non-radioactive isotopes may be achieved in numerous manners, including direct labeling, indirect labeling, and isotope exchange. For example, direct labeling will typically include a chemical reaction of an isotope with a chemical group within the labeled cell (such as an iodine reaction with a tyrosine or histidine group of a protein). Alternatively, or additionally, the radioisotope may also be taken up into a cell via a specific transporter (for the isotope or a compound that includes the isotope).

On the other hand, and especially where the radioisotope is not readily reactive with a cellular component, the radioisotope can be bound ex vivo to a carrier, and especially a chelator, which may then have a reactive group that attaches to a component of a cell. Of course, it should be appreciated that the chelator will also increase the molecular mass of the radiolabel and as such will reduce or entirely prevent leakage of the label from the cell. Where the chelator has a reactive group, all known reactive groups are deemed suitable for use herein and especially include thiol reactive groups and amino reactive groups. Therefore, radiolabels may be coupled to a chelator that is then functionalized with a reactive group such as maleimide group, a thiol group, etc.

In further indirect labeling methods, the radiolabel may also be coupled to an affinity reagent that specifically binds to an external component of a cell or to a component that is internalized into a cell. Therefore, especially suitable affinity reagents include antibodies and fragments thereof (e.g., scFv, Fab, etc.) and lectins.

In still further contemplated radioisotope labeling methods, it should be appreciated that the radioisotope may be part of a metabolite, and particularly of an anabolic metabolite. As such it should also be noted that depending on the type of metabolite, the radiolabel may accumulate preferentially in a specific cell compartment of class of compounds. For example, suitable labeled metabolites include various lipids, and especially membrane-type lipids, amino acids and proteins, phosphates, carbohydrates (particularly carbohydrates of the glycocalyx), nucleotides, etc.

Labeling may also be performed in a passive and less directed manner, and especially contemplated methods include isotope exchanges. For example, where labels include deuterium tritium, nitrogen, and/or oxygen isotopes, the cells can be grown in a medium containing heavy water, oxygen-isotope enriched water, isotope enriched ammonium salts/compounds, etc., which will nonspecifically exchange the labeled portion with unlabeled (e.g., proton or hydroxide exchange).

Rare Earth Metals

In other examples, combinations of rare earth metals may be added to the biological sample or therapeutic. Rare earth metals may include neodymium (Nd), yttrium (Y), dysprosium (Dy), lanthanum (La), europium (Eu), terbium (Tb), cerium (Ce), praseodymium (Pr), scandium(Sc), lutetium (Lu), gadolinium (Gd), ytterbium (Yb), samarium (Sm), erbium (Er), thulium (Tm), holmium (Ho), and promethium (Pm). For detection of rare earth metals or isotopes, any suitable assay may be used, including mass spectrometry (e.g., inductively coupled plasma—mass spectrometry (ICP-MS)) or any other suitable measurement device. For example, ICP-MS may be used for the detection of rare earth metals as low as one part per trillion. Such techniques separate ions by their mass to charge ratio, allowing the detection of different isotopes.

Alternatively, or additionally, rare earth based labeling may also take advantage of the characteristic optical properties (especially fluorescence) of quantum dots that contain rare earth elements. Nanocomposite quantum dots can even be tuned by composition to specific wavelengths of absorption and emission. On the other hand, many rare earth metals are also readily chelated by various multi-dentate ligands, which may advantageously help retain the rare earth metal chelate within the intracellular space.

Primers

In still other aspects, one or more modified primers may be added to the biological deposit. The modified primers may be assayed (e.g., detection using a DNA hybridization assay) to identify the deposit. In this case, primers may be modified to be resistant to DNAse within the cell, in order to be suitable as an identifier of a biological deposit.

In other cases, primers may be encapsulated within a nanoliposome and the liposome may be transfected into the cell. Encapsulation may help protect the primers from degradation within the cell, and may help ensure uniformity of the types of primers passed to daughter cells during cell passage. Moreover, in further preferred aspects of the inventive subject matter, the primers and/or oligonucleotides (and variants thereof) can be enclosed in mitochondria to so isolate the primers and/or oligonucleotides to a specific compartment and to so help avoid adverse interaction of the primers and/or oligonucleotides with transcription and/or translation in a cell.

Dyes

In other example, colorimetric or fluorescent dyes (e.g., such as CellBrite™ dyes) may be used to track biological deposits. In some cases, membrane dyes may be used, such as fluorogenic membrane dyes that covalently stain the plasma membrane or covalently label cell surface proteins. These dyes are available in a wide variety of bright and phosphostable colors and are non-toxic to the cell. In this case, a biological deposit or third party product may be tested for the presence of different combinations of dyes present on the cell surface to identify the biological material. For example, the biological sample may be validated by spectral analysis to validate fluorescent dyes.

Transfection of Large Cargo Using PbAE

In another aspect, exogenous mitochondria may be used to tag the biological deposit (e.g., cell lines). Any suitable transfection method may be used to transfect cells with mitochondria, including but not limited to PASTE, BLAST, etc. In another aspect, poly($\beta$-amino ester) PBAE may be used to transfect mitochondria with a high (near 100%) viability.

U.S. patent application publication 2020/0009259, which claims priority to provisional application 62/695,457, which covers PBAE techniques, is incorporated by reference in its entirety herein. Briefly, this application covers methods of transfecting cells with a cargo, comprising forming a complex of the cargo with a poly(beta amino ester) (PBAE) molecule, mixing the complex with an isotonic buffer, and contacting the complex with the cells, wherein the cargo has a dimension of at least 0.5 µm. The PBAE molecule may be formed by reacting an amine with a di(acrylate ester). In some aspects, the PBAE molecule is poly(1,4-butanediol diacrylate-co-4-amino-1-butanol). In some aspects, the PBAE molecule is capped with 1-(3-aminopropyl)-4-methylpiperazine. In some aspects, the concentration of PBAE may be from about 1.0 to about 20 mg/ml, from about 1.0 to about 10 mg/ml, or from about 1.0 to about 5.0 mg/ml. In other aspects, the cargo is mitochondria, a protein, an exosome, an organelle, or a tumor antigen having at least one dimension that is at least 0.5 µm.

In some aspects, mitochondria from any origin (e.g., endogenous, genetically engineered, etc.) may be transfected into recipient cells using the methods provided herein. Mitochondria may be isolated from any suitable tissue, including but not limited to liver, kidney, skeletal muscle, neurons, retina, cardiac muscle, etc. Commercially available kits are available for isolating mitochondria from tissue.

Mitochondria may be isolated from any suitable species including but not limited to *Homo sapiens, Bos Taurus, Mus musculus, Xenopus laevis, Plecoglossus altivelis, Pan paniscus, Gorilla gorilla, Lemur catta, Cebus albifrons, Tarsius bancanus, Hylobates lar, Rattus norvegicus, Pogona vitticeps, Bufo marinus*, etc. In some cases, the mitochondria to be transfected may be fully functional/active, in other cases, the mitochondria may be inactive or defective, etc.

Of course, it should be appreciated that the mitochondria suitable for use herein may themselves be further modified either by addition of a label (e.g., nucleic acid, radiolabel, dye, etc.) or via cultivation in an environment that will pervasively label the mitochondria (e.g., cells grown in media containing radioactive phosphate, $D_2O$, nutrients with enhanced $^{13}C:^{12}C$ ratio, etc. Therefore, thusly cultivated cells will contain modified mitochondria that are distinct from the host cell's mitochondria.

Any suitable target comprising a membrane may be transfected with mitochondria, including, but not limited to, bacteria, yeast, viruses (e.g., Adv5, Polio, etc.), exosomes, etc. In some cases, the transfected viruses or exosomes may act as vaccine vehicles for vaccine delivery.

Cells may be tagged with a single type of mitochondria or with multiple types of mitochondria to create a unique profile. In some cases, specific mitochondria for specific biological deposits may be used and the mitochondria "species" may be mapped to a vile and/or stored in a database. In this approach, if mitochondria become nonfunctional or inactive, the cells may degrade the mitochondria. In general, these techniques are suitable when deposited biological material does not include modifications to mitochondrial DNA.

In some aspects, mitochondria is specific to an organism. For example, mitochondria from a first organism may have a first signature, mitochondria from a second organism may have a second signature, etc. Thus, the mitochondria may be mixed together to generate different types of unique tags for cells. In other aspects, modified mitochondria may be used to tag cell samples (e.g., decorating mitochondria with key tags, engineering mitochondria with specific sequences, etc.).

In other aspects, downgraded or degraded mitochondria may be used to reduce the ability of cells to proliferate. In some aspects, proteins involved in mitochondrial function may be modified to cause impairment, including, but not limited to, proteins involved in oxidative phosphorylation, ubiquinone biosynthesis, the citric acid cycle, etc. to cause impairment. This approach may make commercial use of the biological material difficult as the cells may not be able to replicate to a desired concentration within a given timeframe, leading to low yield.

Alternatives to mitochondria include, but are not limited to, organelles, liposomes, exosomes (inert exosomes), etc., or any large cargo suitable for transfection with PBAE techniques.

Yet another type of cargo that could be delivered to the cells include nanoparticles that are tagged with barcodes. In some embodiments, the barcodes include DNA-based barcodes where the DNA does not interact with the cellular biologic to any significant degree. Examples of DNA barcodes that can be leveraged with the disclosed techniques are described in international patent application WO2019089561, herein incorporated by reference.

Tracking

In some cases, present techniques may be used to track deposited cell lines. In other cases, present techniques may be used to track products of deposited cell lines (e.g., expressed proteins, antibodies, etc.). In the latter case, the products, such as a protein or antibody or other biologic, may incorporate the radioisotopes into the product produced by the tagged cell line. For example, if radioisotopes of carbon, oxygen, phosphorus, nitrogen, or other elements are present in the cell line, then these isotopes may be incorporated into the biological products produced by the deposited cell line. While the ratios of the isotopes in the product may be different from the ratio of isotopes present in the cell line, the types of isotopes present in the cell line and product would correlate, provided that the radioisotopes may be incorporated into the product. For example, a product may contain carbon, oxygen, phosphorus, and nitrogen radioisotopes, as these may be incorporated into a biological product, but would not be expected to contain elements not found in the biological product.

Figure 2:
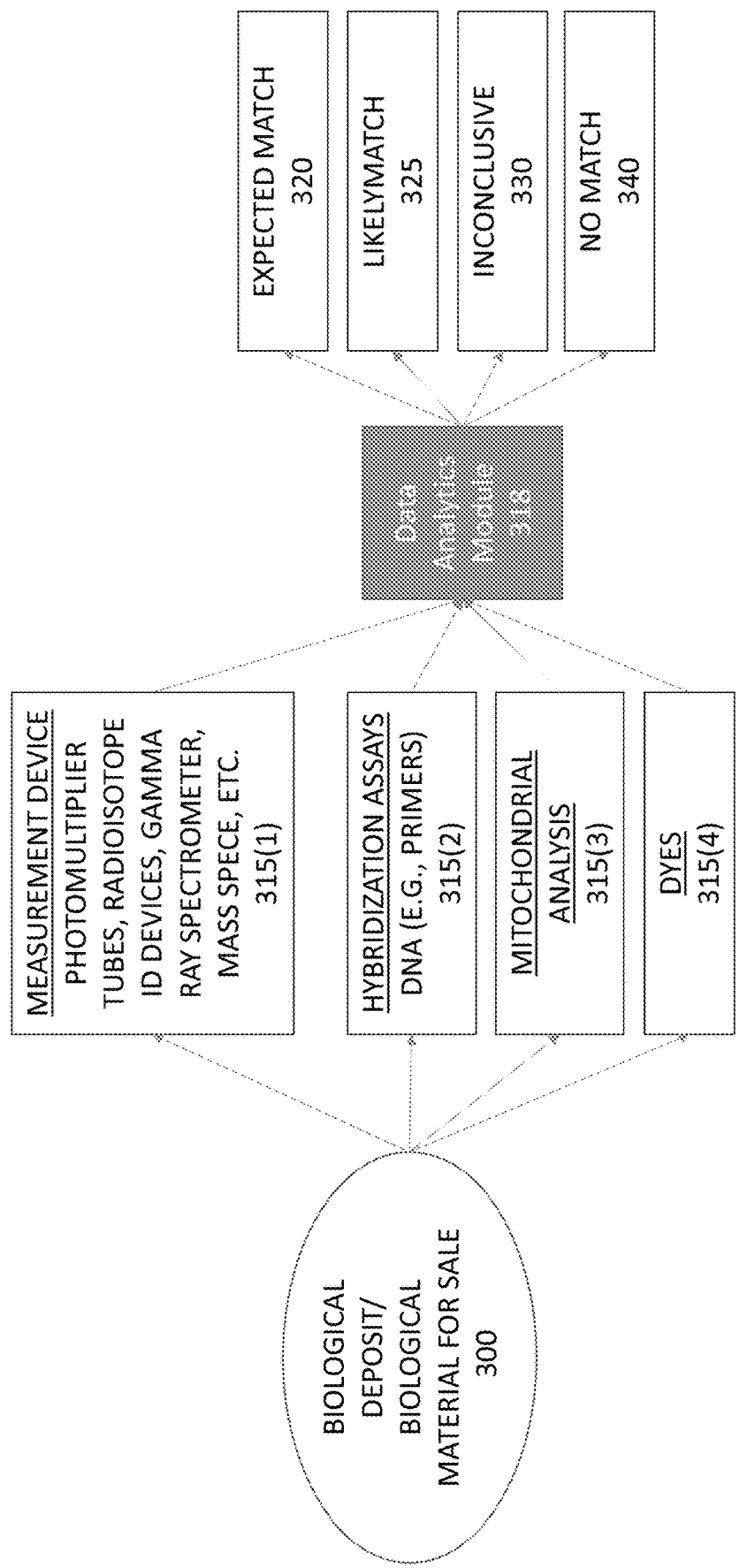
FIG. 2 represents detection techniques of tags and analysis outcomes, according to embodiments of the techniques disclosed herein.

FIG. 2 shows a flow diagram in which a biological deposit/biological material for sale 300 is obtained and undergoes analysis to detect whether tags are present with the biological material. Unique tags or combinations thereof may be added to the biological sample prior to deposit in the repository. The biological sample or a derivative of the biological sample may be later tested for the presence of the tags, which would validate the identity of the biological sample (e.g., by detecting unique tags or combinations of tags present in the biological sample) as from or produced from a known labeled biological material.

The biologic deposit to be assayed may be obtained from the ATCC (e.g., in this case, a competitor may obtain the original ATCC deposit, generate a biological material using the obtained deposit, and may then deposit the biological material, which may be obtained by the owner of the biological deposit) or from a product for sale on the market. The biological deposit/biologic material 300 may be tested for the presence of isotopes. At each step in a logistics chain, material 300 could be tested or measured. The resulting signatures can then be recorded within the database. For example, the resulting signatures can be stored within a distributed ledger, notarized data structure, or blockchain. Such techniques can be adapted from international patent application publication WO2018057520.

Unique tags or combinations of isotopes may include, but are not limited to, one or more primers, one or more rare earth metals, one or more isotopes, one or more types of mitochondria, one or more dyes, etc. In some cases, mitochondria may be tagged with radioisotopes. In some cases, it may be desirable to deliver radioisotopes or other tags encapsulated in nanoparticles to cells of the biologic deposit. One way to achieve this is to attach an aldox linker to the nanoparticle, as the aldox linker may trigger uptake of the nanoparticle into the cell, thereby delivering the tags (isotopes) to the cell. In other cases, for applications of personalized medicine, present techniques may be used to identify a biological deposit tailored to a specific individual or a cohort of individuals.

For example, when a biological sample is deposited to a public repository, one or more tags may be used to label the biological sample to facilitate tracking of the biological sample post deposit. The types of tags (e.g., types of different rare earth metals, types of different isotopes, types of different primers and/or length of primers, etc.) may be determined based on the total number of biological samples stored in the repository.

Various techniques 315(1)-315(4) may be available to analyze the biological deposit, and the selected technique may depend upon the type of tag used to label the biological deposit. For instance, in the case of rare metals or isotopes, measurement device 315(1) may be used to identify the types and amounts of tags present. In the case of primers, hybridization assays 315(2) may be used to identify the types and amount of tags present. In the case of mitochondria, mitochondrial analysis 315(3) may be used to identify the types and amount of tags present. In the case of dyes, colorimetric assays 315(4) may be used to identify the types and amount of tags present. Additional techniques can include live cell interferometry, phase measurement of cell mass, cell sorting, or other techniques. One of skill in the art will appreciate that there are many possible workflow variations in analysis of labeled biological samples, and for a given type of label/tag, any suitable technique known in the art may be used to detect such a label/tag. Present techniques may be used for the entire life cycle of a deposited biological sample, beginning with deposit, continuing through withdrawal of the deposit, and through a subsequent deposit of a biological material generated or derived from the original biological deposit.

Once the sample has been analyzed by the various techniques available for 315, the results of the analysis may be provided to a data analytics module 318 to determine whether a match is found. The data analytics module may compare the analysis results to profiles stored in a database (e.g., a predicted profile generated based upon known half-lives and types of radioisotopes, an experimental profile based upon analysis of the biological sample as a function of time, etc.) to determine if an expected match 320 in terms of types of tags and ratios of respective tags are present. For example, for a biological sample tagged with four different radioisotopes, wherein the radioisotopes are in a specific ratio (e.g., 1:3:5:8 first isotope: second isotope: third isotope: fourth isotope, etc.), the types of radioisotopes and the respective ratios may be determined by any suitable measurement device 315(1) (e.g., photomultiplier tubes, radioisotope identification devices, spectroscopic or portable radiation detectors, gamma ray spectrometer, mass spectrometer, etc.) and the data analytics module 318 may search a database to find one or more potential matches. Thus, for a sample obtained from a deposit and passaged through one or more rounds of cell culture, the types of radioisotopes and ratios of radioisotopes may be searched to identify a corresponding biological deposit.

The system may classify the biological deposit results into one of four categories: expected match 320, likely match 325, inconclusive match 330, or no match 340. An expected match signifies that the types and possibly ratios of the isotopes match an entry in the database. For example, a biological deposit that was labeled with 5 isotopes with a ratio [first isotope 1:second isotope 2: third isotope 1: fourth isotope 2: fifth isotope 1] would receive a match if each and every isotope are found in the database for a single entry. Alternatively, if there are multiple entries in the database, one of which has the observed ratio, then an expected match may be determined. One should appreciate that such matches may take into account the passage of time with respect to the measured ratios to account for different isotope half-lives.

For a likely match 325, a unique subset of the isotopes may be found in the database, but not all of the isotopes (e.g., due to experimental or other environmental complications). For example, analysis may have identified four isotopes that are only present in a single database record, but not all five isotopes. Alternatively, multiple entries in the database may be determined to match all entries in the database with only one entry having isotope ratios similar to, but not exactly, experimentally determined ratios (e.g., from mass spectrometry or any other suitable measurement device). In other cases, the system may determine that no match is found (e.g., due to different isotopes, or no isotopes), while in other cases, the analysis may be inconclusive (e.g., matching two or more entries in the database without being able to distinguish between these entries).

Figure 3A:
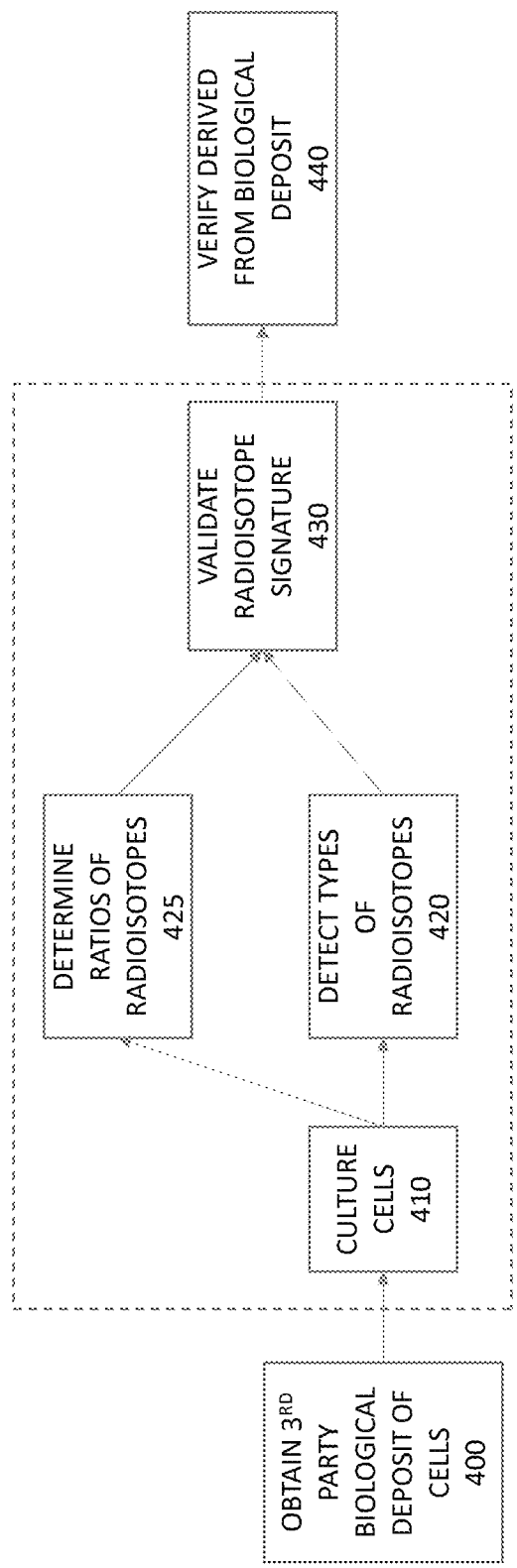
FIGS. 3A and 3B represent example workflows of detecting tags in a cell line (FIG. 3A) or a biological product produced by a cell line (FIG. 3B), according to embodiments of the techniques disclosed herein.

FIG. 3A shows processing of a biological deposit, in this case, a cell line, from a third party to determine whether the cells were derived from a labeled biological deposit. The biological deposit may be obtained at operation 400, and may contain one or more tags (e.g., isotopes, rare earth metals, primers, dyes, etc.), such that the tags or combination thereof is specific to the biological deposit. This flow diagram shows a specific process for testing for the presence of the tags in cell lines.

Once the labeled biological sample is received, the biological sample may undergo an optional culturing step 410 to select for viable cells and increase the cell population. In some cases, this step may be skipped so as not to dilute the amount of tags present in the sample, which may already be low. At operation 420, the sample may be analyzed for the presence of specific types of tags, such as radioisotopes 420. At operation 425, the ratios of radioisotopes may be determined for the sample. Accordingly, in some cases, both the types and ratios of the tags may be detected, to provide a high level of confidence that the biological deposit was generated from a previously labeled deposit. When the types of detected tags match the types of tags in a unique manner from the deposit, at operation 430, the cell line from the third party is validated to match the deposit at operation 440.

Figure 3B:
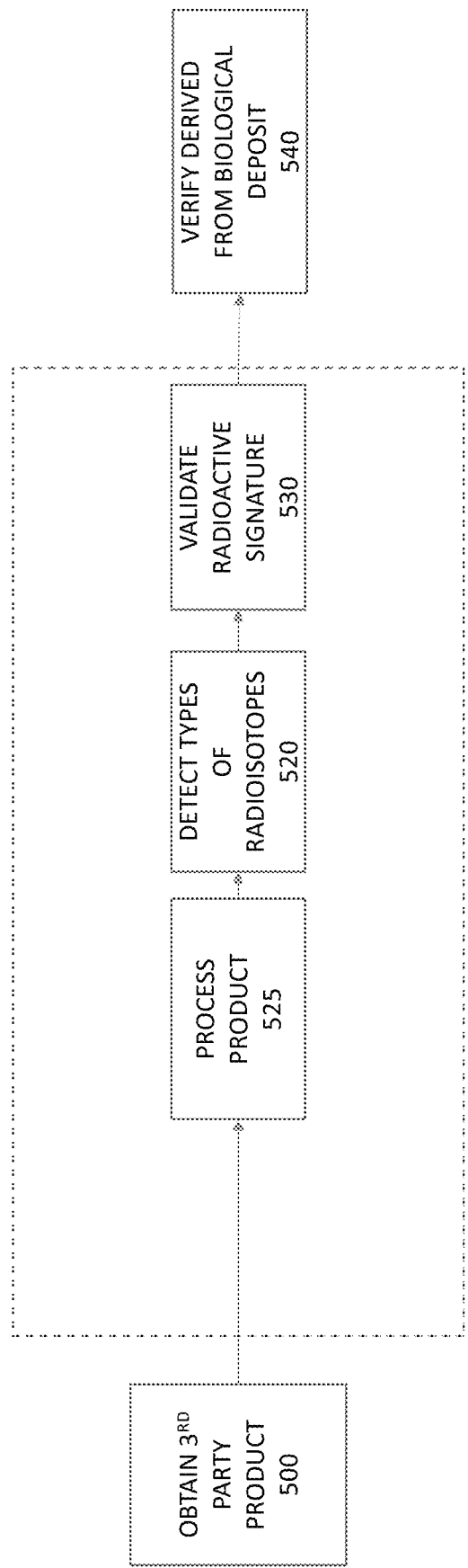

FIG. 3B shows processing of a biological product, in this case, a product of cell line from a third party to determine whether the product was produced from a labeled biological deposit. At operation 500, the product is obtained. At operation 525, the product may undergo processing to purify or otherwise prepare the product for further analysis. For example, if the product is a lyophilized antibody, the antibody may undergo resuspension and filtration prior to analysis. At operation 520, the product is tested for the presence of different types of radioisotopes. If the types of radioisotopes in combination are unique, the radioisotope signature may be validated by identifying a matching entry in the database at operation 530. At operation 540, the biological deposit may be validated as having been derived from a biological deposit from another source (not the third party from which the product was obtained).

FIG. 4 shows an example of an isotope decay profile. Three different isotopes are shown, each with different decay rates and different initial concentrations. At time T1, the ratio of the three isotopes are about 1:10:15 while at time T2 the ratio of the three isotopes are about 1:2:4. Accordingly, this example shows how the ratios may change as a function of time.

FIG. 5 shows a flow chart of example operations of tracking a biological deposit (deposited biological sample).

At operation 710, a biological sample is deposited into a public repository, while possibly notarizing the deposit via making an entry into a notarized ledger (e.g., blockchain, distributed ledger techniques, hash graph, etc.) wherein the deposited biological sample is associated with one or more tags that uniquely identify the biological sample among a population of deposited biological samples. At operation 715, a profile is stored in a database comprising types of the one or more tags and/or respective ratios of the one or more tags for the deposited biological sample. At operation 720, a test biological sample is obtained and analyzed for the presence of one or more tags. At operation 725, the database is queried to determine whether the one or more tags from the test biological sample match the profile of the deposited biological sample. At operation 730, when the one or more tags from the test biological sample match the one or more tags of the deposited biological sample, the test biological sample is validated to have been produced or derived from the deposited biological sample.

It should be noted that any language directed to a computer or computing device should be read to include any suitable combination of computing devices, including servers, interfaces, systems, appliances, databases, agents, peers, engines, controllers, modules, or other types of computing devices operating individually, collectively, or cooperatively. One of ordinary skill in the art should appreciate that the computing devices comprise one or more processors configured to execute software instructions that are stored on a tangible, non-transitory computer readable storage medium (e.g., hard drive, FPGA, PLA, PLD, solid state drive, RAM, flash, ROM, external drive, memory stick, etc.). The software instructions specifically configure or program the computing device to provide the roles, responsibilities, or other functionality as discussed below with respect to the disclosed apparatus. Further, the disclosed technologies can be embodied as a computer program product that includes a tangible, non-transitory computer readable medium storing the software instructions executable by a processor to perform the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as structure including one or more processors or cores of the computing element being programmed by a set of software instructions stored in the memory of the computing element to execute the set of functions on target data or data objects stored in the memory.

The discussion herein provides many example embodiments of the subject matter described herein. Although each embodiment represents a single combination of elements, the subject matter described herein is considered to include all possible combinations of the disclosed elements. Thus if one embodiment comprises elements A, B, and C, and a second embodiment comprises elements B and D, then the subject matter described herein is also considered to include other remaining combinations of A, B, C, or D, even if not explicitly disclosed. Further, the term of the form "at least one of A, B, and C" should be interpreted as any combination of elements alone or in combination unless otherwise excepted.

It should be apparent to those skilled in the art that many more modifications besides those already described are possible without departing from the concepts presented herein. The disclosed subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A method of tracking a biological deposit, the method comprising:
   depositing a biological sample into a public repository, wherein the deposited biological sample comprises two or more tags selected from the group consisting of isotopes, rare earth metals, and mitochondria, and wherein the tags uniquely identify the biological sample among a population of deposited biological samples;
   determining a ratio of the two or more tags of the deposited biological sample
   storing, in a database, a profile comprising the tags for the deposited biological sample;
   obtaining a test biological sample and analyzing the test biological sample for the presence of two or more tags;
   determining a ratio of the two or more tags of the test biological sample
   querying, using a processor, the database to determine whether the ratio of the two or more tags from the test biological sample match the ratio of the two or more tags of the deposited biological sample; and
   upon matching the ratio of tags, validating that the test biological sample is produced or derived from the deposited biological sample.

2. The method of claim 1, further comprising:
   validating that the test biological sample is derived from the deposited biological sample when at least three types of tags of the test biological sample uniquely match the profile, wherein said profile is in a database of profiles.

3. The method of claim 1, wherein the tags comprise at least three rare earth metals.

4. The method of claim 1, wherein the tags comprise at least three isotopes.

5. The method of claim 1, further comprising:
   detecting the types of tags and the ratios of tags of the test biological sample with a measurement device; and
   determining whether the detected types of tags and the ratios of the tags match the profile of the deposited biological sample.

6. The method of claim 1, further comprising:
   detecting the types of tags of the test biological sample with nucleic acid hybridization; and determining whether the detected types of tags of the test biological sample match the profile of the deposited biological sample.

7. The method of claim 1, wherein at least one of the two or more tags is mitochondria.

8. A method of tracking a biological deposit, the method comprising:
   obtaining a test biological sample and analyzing the test biological sample for the presence of two or more tags, wherein the two or more tags are selected from the group consisting of isotopes, rare earth metals, and mitochondria;
   determining a ratio of the two or more tags of the test biological sample;
   querying, using a processor, a database to determine whether the ratio of the two or more tags from the test biological sample match profiles stored in a database, wherein each profile contains ratio of two or more tags of a deposited biological sample; and
   upon matching the ratio of tags from the test biological sample with the ratio of tags of the deposited biological sample, validating that the test biological sample is produced or derived from the deposited biological sample.

9. The method of claim 8, further comprising:
   when at least three types of tags of the test biological sample uniquely match the tags of a profile, validating that the test biological sample is derived from the deposited biological sample.

10. The method of claim 8, wherein the tags are selected from the group consisting of isotopes, primers, dyes, rare earth metals, and mitochondria.

11. The method of claim 8, further comprising:
   detecting the types of tags and the ratios of tags of the test biological sample with a measurement device; and
   determining whether the detected types of tags and the ratios of the tags match the profile of the deposited biological sample.

12. The method of claim 8, further comprising:
   detecting the types of tags of the test biological sample with nucleic acid hybridization; and
   determining whether the detected types of tags of the test biological sample match the profile of the deposited biological sample.

* * * * *